United States Patent [19]

Kornfeld et al.

[11] 4,201,862

[45] May 6, 1980

[54] 2-AZAERGOLINES AND 2-AZA-8(OR 9)-ERGOLENES

[75] Inventors: Edmund C. Kornfeld; Nicholas J. Bach, both of Indianapolis, Ind.

[73] Assignee: Eli Lilly and Company, Indianapolis, Ind.

[21] Appl. No.: 21,055

[22] Filed: Mar. 16, 1979

[51] Int. Cl.² .............................................. C07D 471/06

[52] U.S. Cl. .......................................... 546/67; 546/69; 424/261

[58] Field of Search ..................................... 546/67, 69

Primary Examiner—Mary C. Lee
Attorney, Agent, or Firm—James L. Rowe; Arthur R. Whale

[57] ABSTRACT

2-Azaergolines, 2-aza-8(or 9)-ergolenes, neuroleptic agents.

5 Claims, No Drawings

2-AZAERGOLINES AND 2-AZA-8(OR 9)-ERGOLENES

BACKGROUND OF THE INVENTION

Compounds based on the ergoline ring system:

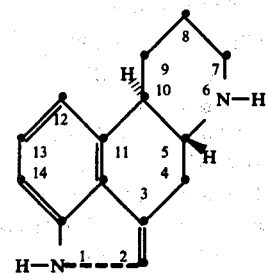

have a suprising variety of physiological actions. For example, many of the amides of lysergic acid, which is D-8β-carboxy-6-methyl-9-ergolene, have valuable and unique pharmacologic properties. The trivial name "ergoline" is given to the above structure and the 9, 10 double bonded compounds related to lysergic acid are called 9-ergolenes rather than 9,10-didehydroergolines. The name D-ergoline or D-8-ergolene or D-9-ergolene is used herein in naming specific compounds. The letter "D" indicates that the C-5 carbon atom configuration has the asbolute stereochemistry designated as R and that the hydrogen is β—above the plane of the ring system. However, modern usage has tended to omit the "D" on the ground that the newly synthesized ergolines or ergolenes are universally derivatives of natural products such as lysergic acid or elymoclavine, all of which have R stereochemical—"D" series—configuration and in which the stereochemical integrity at C-5 is maintained. It should be understood that all of the compounds or classes of ergolines or ergolenes disclosed herein also have the R stereochemical configuration, whether or not the specific or generic name is preceded by a "D".

Among the pharmacologically active amides of lysergic acid are included the naturally occurring oxytoxic alkaloids (ergocornine, ergokryptine, ergonovine, ergocristine, ergosine, ergotamine, etc.), synthetic oxytocics such as methergine and the synthetic hallucinogen—lysergic acid diethylamide or LSD. The amides of D-6-methyl-8-carboxyergoline, known generically as the dihydroergot alkaloids, are oxytocic agents of lower potency and also lower toxicity than the ergot alkaloids themselves. Recently, it has been found by Clemens, Semonsky, Meites, and their various co-workers that many ergot-related drugs have activity as prolactin inhibitors and are also useful in treating Parkinsonism. References embodying some of the newer findings in the field of ergoline chemistry which form part of the background of this invention, but are not necessarily relevant prior art, include the following: Nagasawa and Meites, *Proc. Soc. Exp't'l. Biol. Med.*, 135, 469 (1970); Lutterbeck et al., *Brit. Med. J.*, 228, (July 24, 1971); Heuson et al., *Europ. J. Cancer*, 353 (1970); *Coll. Czech. Chem. Commun.*, 33, 577 (1968); *Nature*, 221, 666 (1969); Seda et al., *J. Reprod. Fert.*, 24, 263 (1971); Mantle and Finn, id, 441; Semonsky and co-workers, *Coll. Czech. Chem. Comm.*, 36, 2200 (1971) 42, 1209 (1977); Schaar and Clemens, *Endocr.*, 90, 285-8 (1972); Clemens and Schaar, *Proc. Soc. Exp. Biol. Med.*, 139, 659-662 (1972), Bach and Kornfeld, *Tetrahedron Letters*, 3225 (1974), Conodi et al, *J. Pharm. Pharmac.*, 25, 409 (1973), Johnson et al, *Experentia*, 29, 763 (1973); Stone, *Brain Research*, 72, 1977 (1974) Lieberman et al, *J.A.M.A.*, 238, 2380 (1977), Cassady et al *J. Med. Chem.*, 17, 300 (1974), Sweeney et al, *Con. Res.* 35, 106 (1975); Fehr et al, *Helv. Chem. Acta*, 53, 2197 (1970), Bernardi et al, *Il Farmaco-Ed. Sci.*, 30, 789 (1975) and Cassady and Floss, *Lloydia*, 40, 90 (1977). Recently issued patents in the field of ergolines or of lysergic acid derivatives include the following: U.S. Pat. No. 3,923,812, U.S. Pat. No. 3,920,664, U.S. Pat. No. 3,901,894, U.S. Pat. No. 3,929,796, U.S. Pat. No. 3,944,582, U.S. Pat. No. 3,934,772, U.S. Pat. No. 3,954,988, U.S. Pat. No. 3,957,785, U.S. Pat. No. 3,959,288, U.S. Pat. No. 3,966,739, U.S. Pat. No. 3,968,111, U.S. Pat. No. 4,001,242, U.S. Pat. No. 4,122,177, U.S. Pat. No. 4,075,213, U.S. Pat. No. 4,075,212, U.S. Pat. No. 3,985,252, U.S. Pat. No. 3,904,757, U.S. Pat. No. 4,096,265, U.S. Pat. No. 3,752,888, U.S. Pat. No. 3,752,814, U.S. Pat. No. 4,110,339, U.S. Pat. No. 4,054,660. Many other related and older patents can be found in U.S. Patent Office Classification Files 260-256.4 and 260-285.5.

2-Azaergolines and 2-aza-8(or 9)-ergolenes have not heretofore been reported.

SUMMARY OF THE INVENTION

This invention provides 2-azaergolines and 2-aza-8(or 9)-ergolenes of the structure

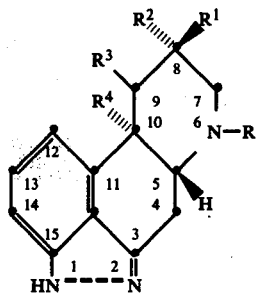

wherein R is H, methyl, ethyl and n-propyl, $R^1$ is $COO(C_1-C_3)$alkyl,

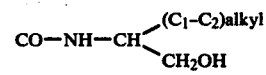

or $CH_2X$ wherein X is $SCH_3$, $SO_2CH_3$, $OCH_3$, Cl, Br, OH, CN, $OSO_2(C_1-C_3)$-alkyl, O-tosyl or $OSO_2$phenyl;

$R^2$, $R^3$ and $R^4$ when taken singly are H, and when taken together as adjacent pairs with the carbon atoms to which they are attached, a double bond, and acid addition salts thereof.

Compounds according to the above formula in which $R^1$ is $COO(C_1-C_3)$alkyl or $CH_2X$ when X is Cl, Br, OH, $OSO_2(C_1-C_3)$alkyl, O-tosyl or $OSO_2$phenyl or in which R is H are useful primarily as intermediates in the preparation of those pharmacologically-active compounds in which R is methyl, ethyl or n-propyl and $R^1$ is

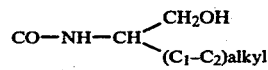

or CH₂X when X is SCH₃, OCH₃, SO₂—CH₃ or CN. Acid addition salts of these pharmacologically active drugs should be formed only with non-toxic acid; i.e., acids whose anions do not contribute materically to the toxicity of the drug.

The acid addition salts of this invention include salts derived from non-toxic inorganic acids such as: hydrochloric acid, nitric acid, phosphoric acid, sulfuric acid, hydrobromic acid, hydriodic acid, nitrous acid, phosphoric acid and the like, as well as salts derived from non-toxic organic acids such as the aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

In the above formula the term "(C₁-C₂)alkyl" includes methyl and ethyl and the term "(C₁-C₃)alkyl" includes in addition n-propyl and isopropyl.

In the above formula, where R², R³ and R⁴ are all hydrogen, the compounds are named as 2-azaergolines. When R² and R³ together with the carbons to which they are attached form a double bond, the compounds are denominated 2-aza-8-ergolenes. Similarly, when R³ and R⁴ define a double bond, the compounds are denominated as 2-aza-9-ergolenes.

It should be noted that the stereochemistry at the three chiral centers, C-5, C-8 and C-10 is specified; i.e., the C-5 hydrogen is beta, the C-10 hydrogen (R⁴), when present, is alpha and the C-8 substituent (R¹) is also beta when there is a 9,10-double bond. (In 8-ergolenes, there is only one substituent at C-8 and it is planar—in the plane of the C-7, C-8, C-9 and C-10 carbons). The compounds represented by formula I above represent one of the two possible trans-fused stereoisomers, the 5β, 10α isomer. Likewise, the substituent at C-8 is always beta—cis to the C-5 hydrogen and trans to the C-10 hydrogen (when present). The stereochemistry can be specified because of the fact that, as will be shown below, the compounds of this invention are synthesized from ergolines or ergolenes which are either derivatives of lysergic acid (a 5β,8β-carboxy-9-ergolene), dihydrolysergic acid, (a trans-5β,10α,8β-carboxyergoline), or elymoclavine, (an 8-hydroxymethyl-trans-5β,10α-8-ergolene). The configuration of these starting materials, which is not affected by the synthetic procedures used herein, has been established and will be signified by the letter "D". A "D" prefix will thus indicate that the C-5 hydrogen is β, and the C-10 hydrogen (when present) is α.

The systematic name for compounds represented by I above is more complex. For example, D-6-methyl-8β-(methylthio)methyl-2-azaergoline (I in which R is CH₃, R¹ is CH₂—S—CH₃ and R², R³ and R⁴ are H), would be named systematically as (6aR, 9β-trans)-4,6,6a,7,8,9,10,-10a-octahydro-7-methyl-9-[(methylthio)methyl]indazolo[4,3-f,g]quinoline. The numbering of the indazolo[4,3-f,g]quinoline ring system is given in II below

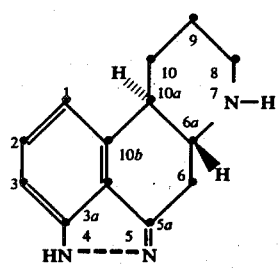

Illustrative compounds coming within the scope of this invention include:

D-6-ethyl-8β-methoxymethyl-2-azaergoline oxalate

D-6-n-propyl-8β-(methylthio)methyl-2-azaergoline maleate

D-6-methyl-8-methylsulfinylmethyl-2-aza-8-ergolene

D-6-ethyl-8β-hydroxymethyl-2-aza-9-ergolene phosphate

N-(2-hydroxy-1-methyl)ethyl D-6-methyl-2-aza-9-ergolene-8β-carboxamide

N-(2-hydroxy-1-ethyl)ethyl D-6-n-propyl-2-aza-8-ergolene-8-carboxamide

Ethyl D-6-methyl-2-aza-9-ergolene-8β-carboxylate

D-6-ethyl-8β-cyanomethyl-2-azaergoline

D-6-n-propyl-8-chloromethyl-2-aza-8-ergolene tartrate

D-6-n-methyl-8-p-tosyloxymethyl-2-aza-8-ergolene oxalate and the like.

DETAILED DESCRIPTION OF THE INVENTION

The preparation of the compounds of this invention involves as a fundamental step the conversion of the indole ring system of an ergoline or an 8(or 9)-ergolene to a 2-azaergoline or 2-aza-8-(or 9)-ergolene containing a pyrazole ring. This reaction sequence is illustrated below.

Reaction Scheme I

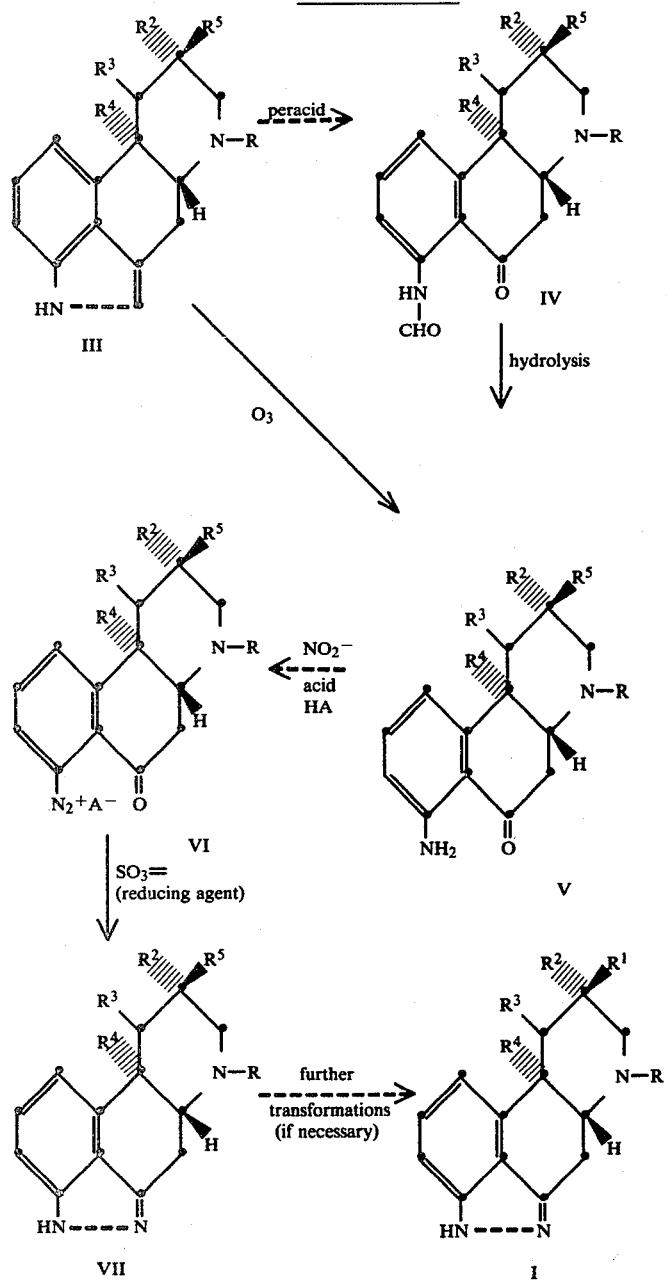

In the above reaction scheme R, $R^2$, $R^3$, and $R^4$ have the same meaning as hereinabove and $R^5$ represents those members of $R^1$ as defined as hereinabove which are not susceptible to either oxidation or bisulfite reduction. Thus $R^5$ includes $COO(C_1-C_3)$alkyl,

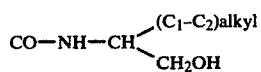

or $CH_2X$ where X is $SO_2CH_3$, $OCH_3$, Cl, Br, OH, CN, $OSO_2$—$(C_1-C_3)$alkyl, O-tosyl or O—$SO_2$-phenyl. HA represents a strong mineral acid.

According to the above reaction scheme, an ergoline, an 8-ergolene or a 9-ergolene represented by formula III is oxidized with a peracid such as sodium periodate, sodium perchlorate, sodium perbromate or the like to a 6-keto-7-quinolinyl formamide (IV). The remainder of the molecule, including the various substituents R, $R^2$, $R^3$, $R^4$ and $R^5$, is not affected by this oxidation. The formamide (IV) can then be hydrolyzed in acid or base to yield the free amine of formula V. Alternatively, the starting ergoline or ergolene of formula III can be ozonized directly to yield the 7-amino-6-ketobenzo[f]quinoline (V). This latter reaction has been carried out by Belalatti et al, Tetrahedron, 33, 1821 (1977) using methyl dihydrolysergate as the substrate. Next the 6-keto-7-amine (V) is diazotized to yield the 6-keto-7-diazonium salt (VI). The diazotization can be carried out by standard procedures involving the use of, for example, sodium nitrite and a strong mineral acid such as hydrochloric acid. t-Butyl and t-amyl nitrites can also be employed in this reaction with equal success. The diazonium salt (VI) is then subjected to reducing conditions which results in the formation of a pyrazole ring and elimination of the 6-keto group. Suitable reducing agents include $SO_2$, bisulfite or sulfite, tin + HCl and the like. The product of this reaction is a 2-azaergoline or a 2-aza-8(or 9)-ergolene in which the various substituent groups have the same meaning as hereinabove. The aza compound (VII) can then be further transformed to yield the compounds of this invention which are not preparable by the above procedure; in particular, the $8\beta$-(methylthiomethyl) derivatives since the $CH_3$—S—$CH_2$ group cannot be present during the peracid or ozone oxidation step but must be formed after the ring opening and ring closure procedure outlined above has been completed. The methylthiomethyl group can, of course, be introduced by replacing a group which $R^5$ represents that can survive the oxidation procedures such as a mesyloxymethyl group.

The starting materials represented by III above are either derivatives of lysergic acid (R is methyl, $R^5$ is ethoxycarbonyl, $R^2$ is H, and $R^3$ and $R^4$ form a double bond), or dihydrolysergic acid (R is methyl, $R^5$ is methoxycarbonyl and $R^2$, $R^3$ and $R^4$ are hydrogen) or elymoclavine (R is methyl, $R^5$ is hydroxymethyl, $R^2$ and $R^3$ form a double bond and $R^4$ is hydrogen.) These starting materials can be further manipulated to produce other groups which $R^5$ represents. Additionally, the methyl group at N-6 can be replaced with ethyl or n-propyl according to standard procedures.

The following illustrates the various transformations of groups at C-8 or at N-6 which can take place either before or after the oxidative ring opening and the reductive ring closing procedures illustrated in reaction scheme I with the aforesaid exception of the methylthiomethyl group which must be introduced after the 2-aza group is already in place. First, using lower alkyl esters of lysergic or dihydrolysergic acid as starting materials, the ester group at C-8 can be reduced with a metal hydride reducing agent such as lithium aluminum hydride in tetrahydrofuran at room temperature to give an $8\beta$-hydroxymethyl group. Other metal hydride reducing agents which can be employed including lithium trimethoxyaluminum hydride, sodium borohydride with aluminum chloride etc. Diethyl ether is also a suitable solvent. Next, the $8\beta$-hydroxymethyl group can be esterified with mesylchloride, a tosylchloride or benzenesulfonylchloride to yield the $8\beta$-mesyloxymethyl, tosyloxymethyl or benzenesulfonyloxymethyl derivative. These sulfonate esters are excellent leaving groups and can be readily replaced by reaction with the sodium salt of methylmercaptan, with sodium methylate or with the sodium salt of methanesulfinic acid to yield the corresponding methylthiomethyl, methoxymethyl or methylsulfonylmethyl derivatives. Alternatively, the hydroxy group of the $8\beta$-hydroxymethyl ergoline or 9-ergolene can be replaced with chlorine or bromine using thionyl chloride, $PBr_3$ and the like to yield the corresponding chloromethyl or bromomethyl derivative. These halogens are also excellent leaving groups and can be readily replaced with any of the above groups employing a sodium salt or by sodium cyanide to yield the corresponding cyanomethyl derivative.

The 6-methyl group present in all of the convenient starting materials and in each of their transformation products can be removed and replaced by an ethyl or an n-propyl group according to the procedure of U.S. Pat. No. 3,920,664, Example 8. According to this procedure, cyanogen bromide alone, or preferably in an inert solvent, is reacted with, for example, D-6-methyl-$8\beta$-hydroxymethyl-9-ergolene to yield the corresponding 6-cyano derivative. Suitable inert solvents for this reaction include chlorinated hydrocarbons such as chloroform, methylenedichloride, carbon tetrachloride, and ethylenedichloride; aromatic hydrocarbons including benzene, toluene or xylene; and polar solvents such as DMA, DMF, and DMSO. The reaction temperature is not critical and temperatures ranging from ambient temperature to the boiling point of the solvent used may be employed. The N-cyano group is readily removed as by reduction with zinc dust in acetic acid, thus producing a secondary amine function (N-H) at N-6. The zinc-acetic acid cleavage of the N-cyano group is usually carried out near the boiling point of the solvent: 100°–120° C. Cleavage of the cyano group can also be accomplished by acidic or basic hydrolysis. In addition, other reducing agents can be employed in place of zinc and acetic acid such as Raney nickel and hydrogen. Alternatively, the N-methyl group can be removed from a 9-ergolene by reaction with a chloroformate such as methyl chloroformate, phenyl chloroformate, benzyl chloroformate, trichloroethyl chloroformate and the like to form an intermediary carbamate, which group can be cleaved to yield the desired 6-nor secondary amine.

Alkylation of the secondary amine with an ethyl, or n-propyl halide, tosylate, etc. is carried out in an inert solvent, preferably a polar solvent such as DMA, DMF, acetonitrile, nitromethane and the like at temperatures in the range 20°–50° C. Suitable bases which may be present in the reaction mixture as acid scavengers include insoluble inorganic bases such as sodium carbonate, potassium carbonate, sodium bicarbonate, sodium hydroxide, and the like, as well as soluble bases such as the tertiary amines, particularly the aromatic tertiary amines like pyridine.

Alternatively, the secondary amine produced by demethylation at N-6 can be acylated in the presence of a tertiary amine base at ambient temperature with acetyl chloride or propionyl chloride to yield the corresponding amide. Reduction of the amide group at N-6 (and of the ester group at C-8 if present as in methyldihydrolysergate simultaneously) by a metal hydride reducing agent such as lithium aluminum-hydride in THF at room temperature yields the corresponding D-6-ethyl (or n-propyl)-$8\beta$-hydroxymethylergoline. If a group is present at C-8 which might react undesirably with the reducing agent, a protecting group can be introduced.

The above ergoline compounds can be prepared from elymoclavine as well as from dihydrolysergic acid, by reduction of the $\Delta^8$ double bond to yield D-6-methyl-$8\beta$-hydroxymethylergoline. The same sequence of reactions for introducing other groups including replacement of the methyl at N-6 with an ethyl or n-propyl group followed by replacement of the hydroxymethyl at C-8 with a methoxymethyl, methylsulfonylmethyl or methylmercaptomethyl group via the intermediate mesylate ester can be carried out as before.

In carrying out transformations at C-8 starting with elymoclavine. Since the hydroxyl of the hydroxymethyl group is an allylic hydroxyl, replacement with chlorine is an available procedure and the allylic chlorine itself is readily replaced by a cyano, methoxy, methylsulfonyl, or methylmercapto group to yield those compounds of this invention in which $R^2$ is hydrogen, $R^3$ and $R^4$ form a double bond, $R^1$ is $CH_2X$ and X is $SCH_3$, $OCH_3$, CN or $SO_2CH_3$. We prefer to use a mixture of triphenylphosphine and $CCl_4$ as the chlorinating agent for the allylic hydroxyl in elymoclavine or 2-azaelymoclavine. Other chlorinating agents can be used such as HCl, HBr, diethylether hydrochloride, a phosphorous trihalide or $POCl_3$, care being taken with these more powerful agents to use reaction conditions which avoid undesirable by-products.

This invention is further illustrated by the following specific examples.

EXAMPLE 1

Preparation of D-6-n-propyl-8β-methoxymethyl-2-azaergoline

One and nine-tenths grams of the methanesulfonate salt of D-6-n-propyl-8β-methoxymethylergoline were dissolved in a 50 ml of methanol and 50 ml of water. This solution was added to a solution containing 2.14 g of sodium periodate in 200 ml of water. The reaction mixture was stirred for about 2¼ hours, after which time it was diluted with aqueous sodium bicarbonate and the resulting alkaline solution thoroughly extracted with chloroform. The chloroform extracts were combined and the combined extracts washed with saturated aqueous sodium chloride and then dried. Evaporation of the chloroform in vacuo yielded a residue comprising N-[1,2a,3,4,4a,5,6,10bα-octahydro-2β-(methoxymethyl)-6-oxo-4-n-propyl-benzo[f]quinolin-7-yl]formamide formed in the above reaction. The compound was purified by chromatography over 35 g of florisil using chloroform containing increasing amounts (1-2%) of methanol as the eluant. Fractions shown by TLC to contain the desired compound were combined and the solvent evaporated from the combined fractions in vacuo. The desired benzoquinoline thus prepared was converted to the maleate salt by dissolving the free base in ether and adding an ethereal solution of maleic acid thereto. Recrystallization of the salt from a methanol-ether solvent mixture yielded 1.10 g of N-[1,2a,3,4,4a,5,6,10bα-octahydro-2β-(methoxymethyl)-6-oxo-4-n-propyl-benzo[f]quinolin-7-yl]formamide maleate melting at 172°-173° C.

Analysis Calc.: C, 61.87; H, 6.77; N, 6.27; Found: C, 61.62; H, 6.91; N, 6.21.

840 mg of the above maleate salt was dissolved in 100 ml of methanol to which was added 100 ml of 10% aqueous sodium hydroxide. The hydrolysis mixture was stirred at ambient temperature for ½ hour and was then diluted with water. The alkaline solution was extracted several times with chloroform and the chloroform extracts combined. The combined extracts were washed with saturated aqueous sodium chloride and then dried. Evaporation of the chloroform yielded 0.62 g of a solid comprised 2β-(methoxymethyl)-4-n-propyl-6-oxo-7-amino-1,2a,3,4,4a,5,6,10bα-octahydro-benzo[f]quinoline as a residue which was recrystallized from methanol and melted at 81°-88° C.

The crystalline amino ketone (2 mmole) was dissolved in a mixture of 10 ml of water and 10 ml of 12 N aqueous hydrochloric acid. The mixture was cooled to a temperature in the range of 0°-5° C. A solution containing 150 mg of sodium nitrite and 5 ml of water was added thereto in dropwise fashion. Next, this diazotization solution was added in dropwise fashion to 50 ml of 7% aqueous sulfurous acid saturated with sulfur dioxide, still employing a reaction temperature in the range 0°-5° C. Gaseous $SO_2$ was also bubbled through the reaction mixture during the reaction. The reaction mixture was left at room temperature for 16¼ hours after which time was made basic with concentrated aqueous sodium hydroxide. The alkaline solution was extracted several times with a mixture of chloroform and isopropanol. The organic extracts were separated and combined. The combined extracts were washed with saturated aqueous sodium chloride and then dried. Evaporation of the solvent yielded a residue comprising D-6-n-propyl-8β-methoxymethyl-2-azaergoline. A chloroform solution of the residue was chromatographed over 30 g of florisil using chloroform containing increasing amounts (2-3%) of methanol as the eluant. Fractions shown by TLC to contain the desired 2-azaergoline were combined and yielded 560 mg of D-6-n-propyl-8β-methoxymethyl-2-azaergoline melting at 256°-258° C. with decomposition. The corresponding mesylate salt melted at 257°-259° C. with decomposition after recrystallization from an ether-methanol solvent mixture.

Analysis Calc.: C, 57.70; H, 7.39; N, 10.62; S, 8.11; Found: C, 57.61; H, 7.23; N, 10.46; S, 8.09.

Following the above procedure, methyl lysergate was oxidized in sodium periodate to form the corresponding 2β-methoxycarbonyl-4-methyl-6-oxo-7-formamido-2,3,4,4a,5,6-hexahydrobenzo[f]-quinoline. The compound melted above 300° C. after recrystallization from methanol and had an IR spectrum plus other physical measurements consistent with the expected structure. Hydrolysis to remove the formyl group followed by diazotization and reduction of the diazonium salt with sulfurous acid yields D-6-methyl-8β-methoxycarbonyl-2-aza-9-ergolene.

Similarily, oxidation of ergonovine maleate yielded N-(2-hydroxy-1-methylethyl)2,3,4,4a,5,6-hexahydro-4-n-propyl-6-oxo-1-formamidobenzo[f]quinolin-2β-yl carboxamide. Removal of the formyl group followed by diazotization of the thus formed amine followed by reduction of the diazonium salt with sulfurous acid yielded N-(2-hydroxy-1-methylethyl)-6-n-propyl-2-aza-9-ergolenyl-8β-yl carboxamide.

EXAMPLE 2

Preparation of 2-Azaelymoclavine

Following the procedure of Example 1, 2.1 g of elymoclavine methane sulfonate and 50 ml of water were added to a solution of 2.6 g of sodium periodate in 200 ml of water. The product was isolated and purified by the procedure of Example 1 involving as a last step the chromatography of the isolated crude product over florisil using chloroform containing increasing amounts (2-5%) of methanol as the eluant. Chromatographic fractions found to contain 3,4,4a,5,6,10bα-hexahydro-2-hydroxymethyl-4-methyl-6-oxo-7-formamidobenzo[f]quinoline formed in the above reaction were combined and the solvent removed therefrom in vacuo. Recrystallization of the residue yielded 3,4,4a,-5,6,10bα-hexahydro-2-hydroxymethyl-4-methyl-6-oxo-7-formamidobenzo[f]quinoline melting at 142°-144° C. with decomposition after recrystallization from a mixture of ether containing a small amount of methanol.

Analysis Calc.: C, 67.12; H, 6.34; N, 9.78; Found: C, 66.91; H, 6.27; N, 9.64.

Still following the procedure of Example 1, 1 g of the above formamido derivative was dissolved in 50 ml of methanol to which were added 50 ml of 10% aqueous sodium hydroxide. The 7-amino compound formed in the above hydrolysis was isolated by the procedure of Example 1; yield=0.70 g. The amino compound (3,4,4a,5,6,10bα-hexahydro-2-hydroxymethyl-6-oxo-7-amino-4-methylbenzo[f]quinoline) was dissolved in 20 ml of 6 N aqueous hydrochloric acid. The acidic solution was cooled in an ice-water bath. A solution 190 mg of sodium nitrite in 5 ml of water was added thereto in dropwise fashion. The resulting solution containing the 7-diazonium chloride formed in the above reaction was added slowly to a solution of 50 ml of 7 N sulfurous acid saturated with $SO_2$ at 0°–5° C. $SO_2$ was bubbled through the reaction during the time of addition and for 15 minutes thereafter. The reaction mixture was kept at room temperature overnight and then made basic with 14 N aqueous ammonium hydroxide. 2-Azaelymoclavine formed in the above reaction was extracted with several portions of a chloroform-isopropanol solvent mixture. The extracts were combined washed with saturated sodium chloride and dried. Evaporation of the solvent yielded a residue containing 2-azaelymoclavine which was purified by chromatography over 30 g of florisil using chloroform containing increasing amounts (2–10%) of methanol as the eluant. Fractions shown by TLC to contain the desired 2-azaelymoclavine were combined. The hydrochloride salt was prepared by dissolving the free base in ethanol and adding an equivalent of ethanolic hydrochloric acid thereto. 2-Azaelymoclavine hydrochloride thus prepared melted at about 280° with decomposition.

Analysis Calc.: C, 61.75; H, 6.22; N, 14.40; Cl, 12.15; Found: C, 61.59; H, 6.19; N, 14.20; Cl, 11.97.

2-Azaelymoclavine thus prepared can be transformed to an active drug by reacting the hydroxymethyl function with thionylchloride in pyridine to form D-6-methyl-8-mesyloxymethyl-2-aza-8-ergolene. Reaction of the thus formed chloride with the sodium salt of methylmercaptan, with sodium methylate, with sodium cyanide or the like yields the corresponding compound according to formula I above in which R is methyl and $R^1$ is $CH_3-S-CH_2$, $CH_3-O-CH_2$, $CN-CH_2$ and the like.

EXAMPLE 3

Preparation of
D-6-methyl-8β-methylthiomethyl-2-azaergoline

One gram of D-6-methyl-8-mesyloxymethylergoline provided by the procedure set forth in Example 6 of U.S. Pat. No. 3,920,664 and 0.2 ml of methanesulfonic acid were dissolved in a 50 ml of methanol. This solution was added to a solution containing 1.3 g of sodium periodate in 100 ml of water. The oxidation mixture was stirred at ambient temperature for 2.75 hours after which time it was diluted with saturated aqueous sodium bicarbonate. The alkaline mixture was extracted several times with chloroform and the chloroform extracts combined. The combined extracts were washed with saturated aqueous sodium chloride and then dried. Evaporation of the solvent in vacuo yielded a residue comprising N-[1,2,3,4,4a,5,6,10bα-octahydro-2β-(mesyloxymethyl)-6-oxo-4-methylbenzo[f]quinolin-7-yl]formamide formed in the above reaction. The compound was purified by chromatography over 35 g of florisil using chloroform containing increasing amounts (1–5%) of methanol as the eluant. Fractions shown to contain the desired compound by TLC were combined and the solvent removed therefrom in vacuo. N-[1,2,3,4,4a,5,6,-10bα-octahydro-2β(mesyloxymethyl)-4-methyl-6-oxobenzo[f]quinolin-7-yl]formamide thus obtained was crystallized from ether: melting point=14-5°–146° C.

Analysis Calc.: C, 55.72; H, 6.05; N, 7.64; S, 8.75; Found: C, 55.78; H, 6.16; N, 7.46; S, 8.72.

815 mg of N-[1,2,3,4,4a,5,6,10bα-octahydro-2β(mesyloxymethyl)-4-methyl-6-oxobenzo[f]quinolin-7-yl]formamide were suspended in 50 ml of methanol. 50 ml of 10% aqueous sodium hydroxide were added thereto. The hydrolysis mixture was stirred at room temperature under a nitrogen atmosphere for 1.75 hours. The reaction mixture was diluted with water and the diluted mixture extracted several times with chloroform. The chloroform extracts were combined and the combined extracts washed with saturated aqueous sodium chloride and then dried. Evaporation of the chloroform left a residue of 650 mg of 2β-mesyloxymethyl-4-methyl-6-oxo-7-amino-1,2,3,4,4a,5,6,10bα-octahydrobenzo[f]quinoline. The compound was recrystallized from ether and melted at 139°–140° C.

Analysis Calc.: C, 56.79; H, 6.55; N, 8.28; S, 9.47; Found: C, 56.74; H, 6.44; N, 8.12; S, 9.21.

2.6 g of 2β-(mesyloxymethyl)-4-methyl-6-oxo-7-amino-1,2,3,4,4a,5,6,10bα-octahydrobenzo[f]-quinoline were dissolved in a mixture of 25 ml of water and 25 ml of 12 N aqueous hydrochloric acid. The acidic solution was cooled in an ice-water bath. A solution of 570 mg of sodium nitrite in 15 ml of water was added thereto in dropwise fashion. After the sodium nitrite had been added, the resulting solution was added rapidly in portions to 125 ml of 7% aqueous sulfurous acid saturated with $SO_2$ at a temperature in the range 5°–7° C. $SO_2$ was bubbled into the reaction mixture during the addition and for an additional 15 minutes. The reaction mixture was allowed to remain at ambient temperature for 24 hours after which time it was poured over ice. The acidic solution was made basic by the addition of 10% aqueous sodium hydroxide. The resulting alkaline mixture was extracted several times with a chloroform-isopropanol solvent mixture. The organic extracts were combined and the combined extracts washed with saturated aqueous sodium chloride and then dried. Evaporation of the solvent yielded a residue comprising D-6-methyl-8β-mesyloxymethyl-2-azaergolene melting at 183°–185° C. with decomposition after recrystallization from methanol.

Analysis Calc.: C, 57.29; H, 6.31; N, 12.53; S, 9.56; Found: C, 57.35; H, 6.33; N, 12.25; S, 9.35.

1.5 g of methylmercaptan were dissolved in 100 ml of dimethylformamide and the solution cooled in an ice-water bath. 1.5 g of sodium hydride as a 50% suspension in mineral oil was added thereto in portions. After the addition of the sodium hydride had been completed, a solution of 1 g of D-6-methyl-8β-mesyloxymethyl-2-azaergoline in 50 ml of DMF was added rapidly in dropwise fashion. The cooling bath was removed and the reaction mixture stirred for 1.75 hours at ambient temperature. The reaction mixture was then diluted with water and the aqueous mixture extracted several times with ethyl acetate. The ethyl acetate extracts were separated and the combined extracts washed with saturated aqueous sodium chloride and then dried. Evaporation of the solvent yielded as a residue D-6-methyl-8β-(methylthiomethyl)-2-azaergoline formed in the above reaction. The compound was purified by chromatography over florisil using chloroform containing increasing amounts (0–3%) of methanol as the eluant. Fractions shown by TLC to contain the desired compound were combined and the solvent evaporated from the combined fractions. The resulting residue comprising purified D-6-methyl-8β-(methylthiomethyl)-2-azaergoline melted at 218°–221° C. with decomposition. The free base was suspended in 10 ml of hot methanol and 0.15 ml of methanesulfonic acid and 5 ml of methanol was added thereto. The mixture was heated until solution occurred. The solution was then allowed to cool to room temperature. D-6-methyl-8β-(methylthiomethyl)-2-azaergoline methane sulfonate salt melted at about 290° C. with decomposition (90% yield).

Analysis Calc.: C, 53.24; H, 6.57; N, 10.96; S, 16.72; Found: C, 53.44; H, 6.59; N, 10.68; S, 16.66.

As previously stated the compounds of this invention have utility as neuroleptic agents. This activity is demonstrated by the ability of the compounds to block a syndrome in mice characterized by explosive stereotyped jumping produced by administration of D-amphetamine and L-DOPA. According to this procedure, D-amphetamine is injected into the mice by the intraperitoneal route at a rate of 3 mg/kg. After 15 minutes, saline is injected subcutaneously followed by L-DOPA injected intraperitonealy at a rate of 300 mg/kg. Ten minutes after the injection of the L-DOPA, the number of jumps are counted for a period of 30 minutes. In testing a drug for neuroleptic activity, the drug is injected in place of saline in the above protocol at various rates. The following table illustrates the results of the determination of the ability of these compounds to block the stereotyped jumping. In the table column 1, gives the name of the compound, column 2 the dose, column 3 the total number of jumps, column 4 the mean jumps per mouse±the standard error and column 5 the percentage inhibition of jumping.

The known neuroleptic drug, haloperidol, in the same test gives a 70% percent inhibition of jumping at 0.3 mg/kg level and an 82% inhibition at a 1 mg/kg level.

Table

| Name of drug | Dose in mg/kg | Total jumps | Mean jumps per mouse ±S.E. | % Inhibition |
|---|---|---|---|---|
| D-6-methyl-8β-(methylthiomethyl)-2-azaergoline methane sulfonate | control | 9821 | 818 ± 153 | |
| | 8 | 5113 | 426 ± 117 | 47.9% |
| | control | 12099 | 1008 ± 232 | |
| | 10 | 6096 | 508 ± 191 | 44.6% |

We claim:
1. A compound of the formula

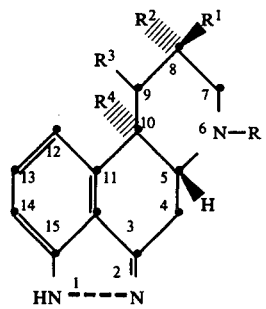

wherein R is H, methyl, ethyl and n-propyl, $R^1$ is $COO(C_1-C_3)alkyl$,

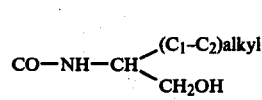

or $CH_2X$ wherein X is $SCH_3$, $SO_2CH_3$, $OCH_3$, Cl, Br, OH, CN, $OSO_2(C_1-C_3)$-alkyl, O-tosyl or $OSO_2phenyl$;

$R^2$, $R^3$ and $R^4$ when taken singly are H, and when taken together as adjacent pairs with the carbon atoms to which they are attached, a double bond, and acid addition salts thereof.

2. A compound according to claim 1 in which $R^1$ is $COO(C_1-C_3)alkyl$ or $CH_2X$ when X is Cl, Br, OH, $OSO_2(C_1-C_3)alkyl$, O-tosyl or $OSO_2phenyl$ or in which R is H.

3. A compound according to claim 1 in which R is methyl, ethyl or n-propyl and $R^1$ is

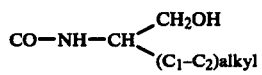

or $CH_2X$ when X is $SCH_3$, $OCH_3$, $SO_2$—$CH_3$ or CN and salts thereof formed with pharmaceutically-acceptable acids.

4. A compound according to claim 3, said compound being D-6-methyl-8β-(methylthiomethyl)-2-azaergoline.

5. The process which comprises reacting a compound of the formula:

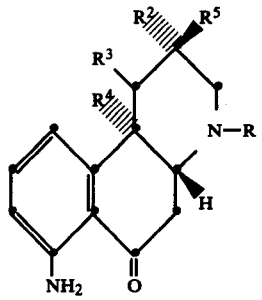

wherein R is methyl, ethyl or n-propyl; $R^2$, $R^3$ and $R^4$ when taken singly are H, and when taken together as adjacent pairs with the carbon atoms to which they are attached, a double bond and $R^5$ is $COO(C_1-C_2)alkyl$,

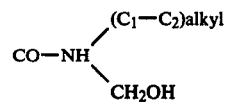

or $CH_2X$ wherein X is $SO_2CH_3$, $OCH_3$, Cl, Br, OH, CN, $OSO_2(C_1-C_3)alkyl$, O-tosyl or O-$SO_2phenyl$, with nitrite in the presence of a strong mineral acid, HA to form a diazonium salt of the structure

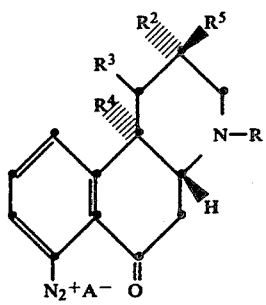
wherein R, R², R³, R⁴ and R⁵ have the same meaning as hereinabove and A⁻ is the anion of a strong mineral acid and then reacting said diazonium salt with a reducing agent to yield a compound of the formula
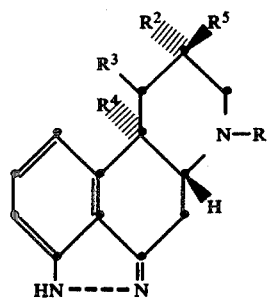
wherein R, R², R³, R⁴ and R⁵ have the same meaning as hereinbefore.
* * * * *